(12) United States Patent
Lipshutz et al.

(10) Patent No.: US 6,280,950 B1
(45) Date of Patent: Aug. 28, 2001

(54) NUCLEIC ACID AFFINITY COLUMNS

(75) Inventors: Robert J. Lipshutz, Palo Alto; MacDonald S. Morris, San Jose; Mark S. Chee, Palo Alto; Thomas R. Gingeras, Encinitas, all of CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/429,521

(22) Filed: Oct. 28, 1999

Related U.S. Application Data

(63) Continuation of application No. 08/815,395, filed on Mar. 10, 1997, now Pat. No. 6,013,440.
(60) Provisional application No. 60/013,231, filed on Mar. 11, 1996.

(51) Int. Cl.[7] ............... C12Q 1/68; C12P 19/34; C07H 21/04
(52) U.S. Cl. ............ 435/6; 435/91.2; 536/24.3; 536/24.31; 536/24.32
(58) Field of Search .......... 435/6, 91.2; 536/24.3, 536/24.31, 24.32

(56) References Cited

U.S. PATENT DOCUMENTS

| | | |
|---|---|---|
| 5,143,854 | 9/1992 | Pirrung et al. |
| 5,202,231 | 4/1993 | Drmanac et al. |
| 5,437,976 | 8/1995 | Utermohlen |
| 5,527,681 | 6/1996 | Holmes |
| 5,547,839 | 8/1996 | Dower et al. |
| 5,650,274 * | 7/1997 | Kambara et al. .......... 435/6 |
| 5,795,714 * | 8/1998 | Cantor et al. ............ 435/6 |
| 5,800,992 * | 9/1998 | Fodor et al. ............. 435/6 |
| 6,103,463 * | 8/2000 | Chetverin et al. ........ 435/6 |

FOREIGN PATENT DOCUMENTS

| | | |
|---|---|---|
| 392 546 | 10/1990 | (EP). |
| 717 113 | 6/1996 | (EP). |
| WO 88/01302 | 2/1988 | (WO). |
| WO 88/10977 | 11/1989 | (WO). |
| WO 90/03382 | 4/1990 | (WO). |
| WO 93/17126 | 9/1993 | (WO). |
| WO 97/10365 | 3/1997 | (WO). |

OTHER PUBLICATIONS

Duncan et al., "Affinity Chromatography of a Sequence-specific DNA Binding Protein Using Teflon–Linked Oligonucleotides," *Analytical Biochemistry*, 165:104–108 (1988).

Meinkoth et al., "Hybridization of Nucleic Acids Immobilized on Solid Supports," *Analytical Biochemistry*, 138:267–284 (1984).

Research Genetics (an advertisement), *Nuc. Acids Res.*, 22(15), (1994).

* cited by examiner

*Primary Examiner*—Kenneth R. Horlick
(74) *Attorney, Agent, or Firm*—Townsend and Townsend and Crew LLP

(57) ABSTRACT

This invention provides nucleic acid affinity matrices that bear a large number of different nucleic acid affinity ligands allowing the simultaneous selection and removal of a large number of preselected nucleic acids from the sample. Methods of producing such affinity matrices are also provided. In general the methods involve the steps of a) providing a nucleic acid amplification template array comprising a surface to which are attached at least 50 oligonucleotides having different nucleic acid sequences, and wherein each different oligonucleotide is localized in a predetermined region of said surface, the density of said oligonucleotides is greater than about 60 different oligonucleotides per 1 $cm^2$, and all of said different oligonucleotides have an identical terminal 3' nucleic acid sequence and an identical terminal 5' nucleic acid sequences; b) amplifying said multiplicity of oligonucleotides to provide a pool of amplified nucleic acids; and c) attaching the pool of nucleic acids to a solid support.

11 Claims, 1 Drawing Sheet

NUCLEIC ACID AFFINITY COLUMNS

CROSS-REFERENCE TO RELATED APPLICATION

The present application is a divisional of U.S. patent application Ser. No. 08/815,395, filed Mar. 10, 1997, now U.S. Pat. No. 6,013,440 which derives priority from U.S. Provisional Application No. 60/013,231, filed Mar. 11, 1996, the disclosures of which are incorporated by reference.

FIELD OF THE INVENTION

The present invention relates generally to matrices for conducting nucleic acid affinity chromatography. More specifically, the present invention relates to methods of preparing affinity chromatography matrices that bind a plurality of different preselected nucleic acids. The matrices, for example, can bind to substantially every known nucleic acid message in a sample.

BACKGROUND OF THE INVENTION

Affinity chromatography has become a valuable tool for separating biological materials from fluid (typically aqueous) media. Examples include biologically active molecules such as small ligands, proteins, nucleic acids, enzymes, etc.

The basic principle of affinity chromatography involves immobilization of a binding moiety (e.g., a ligand) to an insoluble support. The immobilized binding moiety can then be used to selectively adsorb, e.g., from a fluid medium, the target component(s) (e.g. an enzyme) with which the binding moiety specifically interacts thereby forming a binding moiety/target complex. Elution of the adsorbed component can then be achieved by any one of a number of procedures which result in disassociation of the complex. Thus the specific biologic properties of biological macromolecules can be exploited for purification. The process can be used to isolate specific substances such as enzymes, hormones, specific proteins, inhibitors, antigens, antibodies, etc. on the basis of the biologic specific interactions with immobilized ligands.

Nucleic acid affinity chromatography is based on the tendency of complementary, single-stranded nucleic acids to form a double-stranded or duplex structure through complementary base pairing. A nucleic acid (either DNA or RNA) can easily be attached to a solid substrate (matrix) where it acts as an immobilized ligand that interacts with and forms duplexes with complementary nucleic acids present in a solution contacted to the immobilized ligand. Unbound components can be washed away from the bound complex to either provide a solution lacking the target molecules bound to the affinity column, or to provide the isolated target molecules themselves. The nucleic acids captured in a hybrid duplex can be separated and released from the affinity matrix by denaturation either through heat, adjustment of salt concentration, or the use of a destabilizing agent such as formamide, TWEEN™-20 denaturing agent, or sodium dodecyl sulfate (SDS).

Hybridization (the formation of duplex structure) between two nucleic acid sequences is highly sequence dependent. Sequences have the greatest affinity with each other where, for every purine in one sequence (nucleic acid) there exists a corresponding pyrimidine in the other nucleic acid and vice versa. This sequence dependency confers exquisite specificity on hybridization reactions and permits the preparation of affinity columns that are highly selective for particular target nucleic acids.

Affinity columns (matrices) are typically used either to isolate a single nucleic acid typically by providing a single species of affinity ligand. Alternatively, affinity columns bearing a single affinity ligand (e.g. oligo dt columns) have been used to isolate a multiplicity of nucleic acids where the nucleic acids all share a common sequence (e.g. a polyA).

SUMMARY OF THE INVENTION

This invention provides pools (solutions) of nucleic acids, and nucleic acid affinity matrices that bear a large number of different nucleic acid affinity ligands allowing the simultaneous selection and blocking or removal of a large number of different preselected nucleic acids from a sample. This invention additionally provides methods and devices for the preparation of such affinity matrices.

In one embodiment, this invention provides a method of making a nucleic acid pool (solution of nucleic acids) comprising a plurality of different nucleic acids. The method includes first, providing a nucleic acid amplification template array comprising a surface to which are attached at least 20 oligonucleotides having different predetermined (known) nucleic acid sequences; and second, amplifying the multiplicity of oligonucleotides at least about 10 fold to provide the nucleic acid pool. The oligoncleotides, or subsequences thereof, preferably encode "capture probes" which can be incorporated into an affinity matrix. In a preferred embodiment, each different oligonucleotide is localized in a predetermined region of the surface, the density of the oligonucleotides is preferably greater than about 60 different oligonucleotides per 1 $cm^2$, and the different oligonucleotides preferably have an identical terminal 3' nucleic acid subsequence and an identical terminal 5' nucleic acid subsequence. The 3' and 5' nucleic acid subsequences can be the same as each other or can differ in length and/or nucleotide sequence. The 3' and 5' subsequences preferably flank "unique" central subsequences encoding the capture probes.

The method can further involve attaching the pool of nucleic acids to a solid support to form a nucleic acid affinity matrix.

The template nucleic acids comprising the amplification template can be synthesized entirely using light-directed polymer synthesis or channel methods. Alternatively the template nucleic acids can be synthesized using a combination of methods. For example, in one embodiment, the 3' segments (subsequences) of the template nucleic acids can be synthesized using standard phosphotriester (e.g., phosphoramidite) chemistry. A middle (unique) portion of the template nucleic acids can then be synthesized using light-directed polymer synthesis or mechanically-directed synthesis methods. Finally, the 5' segments (subsequences) of the template nucleic acids can be synthesized using phosphotriester chemistry.

The template nucleic acids can be amplified using any nucleic acid amplification method (e.g. polymerase chain reaction, ligase chain reaction, transcription amplification, etc.). In a preferred embodiment, amplification is by PCR. The template nucleic acids can be released into solution prior to the amplification (e.g. by cleavage of a linker joining the template nucleic acids to the substrate) thereby allowing the amplification to be performed in solution. Alternatively, and in a preferred embodiment, the amplification is performed without releasing the template nucleic acids from the substrate.

In a preferred embodiment, the amplification templates include primer binding regions (e.g. 3' and 5' subsequences flanking the region encoding the capture probe). Preferred amplification templates include identical 3' and 5' primers. The primer binding regions of the amplification template oligonucleotides, and hence the corresponding complementary PCR primers, preferably range in length from about 4 to about 30 nucleotides. The primer binding regions can be identical to each other or can differ in nucleotide sequence and/or in length.

In a particularly preferred embodiment, the region of the amplification templates encoding the capture probes (the non-identical portion of the amplification template(s)) ranges in length from about 6 to about 50 nucleotides. Where it is desired to remove the primer binding regions, they can include a recognition site of a nuclease to facilitate cleavage. In a particularly preferred embodiment, the thermal melting points of the template nucleic acid sequences encoding the capture probes with their complementary sequences varies by less than about 20° C.

In another embodiment, this invention provides for nucleic acid amplification template arrays for practice of the above-described method. In a preferred embodiment, the template arrays comprise a predetermined multiplicity of at least 20 oligonucleotides having different nucleic acid sequences. Each different oligonucleotide is preferably localized in a predetermined region of said surface. The density of the oligonucleotides is preferably greater than about 60 different oligonucleotides per 1 cm$^2$, and the different oligonucleotides have identical terminal 3' nucleic acid subsequences (e.g., primer binding region) and identical terminal 5' nucleic acid subsequences (e.g., primer binding region). The 3' and 5' subsequences can be identical to each other or differ in length and/or nucleotide sequence. The subsequences (primer binding regions) of the oligonucleotides, and hence the corresponding complementary PCR primers, preferably range in length from about 4 to about 30 nucleotides.

The region of the template nucleic acids comprising the amplification template array encoding the capture probe (the "unique" non-terminal subsequence) preferably ranges in length from about 6 to about 50 nucleotides. Where it is desired to remove the primer binding regions, the 3' and/or 5' subsequences can include a recognition site of a nuclease to facilitate cleavage. In a particularly preferred embodiment, the thermal melting points of the template nucleic acid sequences encoding the capture probes with their complementary sequences varies by less than about 20° C.

In another embodiment this invention provides an affinity matrix that removes substantially all known nucleic acid messages in a sample and methods of making such an affinity matrix. In a preferred embodiment, the affinity matrix comprises a multiplicity of at least 20 different predetermined oligonucleotides where, for each nucleic acid message, there exists in the affinity matrix an oligonucleotide complementary to the nucleic acid message or a subsequence thereof. The matrix, however, does not include every possible oligonucleotide having the same length as the predetermined oligonucleotides. The oligonucleotides can be selected such that the affinity matrix includes fewer than 80% of the total number of possible nucleotides, preferably fewer than 60% of the total number of possible nucleotides, more preferably fewer than 40% to the total number of possible oligonucleotides, and most preferably less than about 30% or even 20% or even 10% or even 5% of the total possible number of oligonucleotides having the same length as the predetermined oligonucleotides. Oligonucleotides comprising preferred nucleic acid matrices range in length from about 6 to about 50 nucleotides.

Oligonucleotides for inclusion in such affinity matrices can be selected as described herein by the steps of i) determining an allowable $T_m$ interval, ii) determining a mismatch $T_m$ threshold; iii) identifying all nucleic acid sequences complementary to a known message whose $T_m$ to said message is within the allowable $T_m$ interval; iv) determining the likelihood of each of the nucleic acid sequences complementary to the known message also occurring in an unknown message; v) sorting the sequences in order of likelihood with the least likely sequence first to produce a sorted sequence list; vi) selecting the first nucleic acid sequence in the list whose $T_m$ to all other known messages in the sample is below the mismatch $T_m$; vii) repeating step vi) until a desired number of nucleic acids that specifically hybridize, under stringent conditions, to the known message are obtained; and viii) repeating steps iii) through vii) until at least one nucleic acid sequence that hybridizes specifically under stringent conditions to each known nucleic acid message is selected. Step (vi) can further comprise selecting the probe that additionally has a $T_m$ to all already selected nucleic acids below the mismatch $T_m$.

In one embodiment the allowable $T_m$ interval ranges from about 30° C. to about 80° C. In another preferred embodiment, the mismatch $T_m$ is at least 5° C. lower than the allowable $T_m$ interval. The likelihood can be determined by calculating the probability of occurrence of each of the nucleic acid sequences of step (iii) in a calculated nucleic acid probability distribution. The oligonucleotides can be produced by amplification from a nucleic acid amplification template array as described above and further herein. Further details on the selection of oligonucleotides in the matrix are provided herein.

In still yet another embodiment, this invention provides a nucleic acid affinity matrix that binds to N previously unknown nucleic acid messages and methods of making such nucleic acid matrices. The method involves the steps of first providing a multiplicity of at least N different predetermined oligonucleotides each oligonucleotide complementary to an unknown nucleic acid message predicted to be present in a nucleic acid sample or complementary to a subsequence of the unknown nucleic acid message; and second, attaching the nucleic acids to a solid support. The oligonucleotides can be selected by: i) providing a list of all possible oligonucleotides of length K; ii) deleting from the list all of the oligonucleotides that hybridize to known nucleic acid messages; iii) calculating a probability of occurrence in a nucleic acid distribution of each of the probes remaining in the list; iv) sorting the list from highest probability to lowest probability; v) selecting the highest probability oligonucleotide for inclusion in the affinity matrix; and vi) repeating steps (iii) through (v) until N oligonucleotides are selected. The selection of step (vi)can further comprise recalculating the probability on the condition that probability distribution contains no nucleic acids complementary to those oligonucleotides already selected. Selection step (v) can further include selecting an allowable $T_m$ interval and selecting the highest probability oligonucleotide whose $T_m$ lies within the allowable $T_m$ interval. The oligonucleotides can be amplified from the nucleic acid amplification template arrays described above. In a particularly preferred embodiment, the oligonucleotides are attached to a solid support (e.g. glass beads) by a covalent linkage to a biotin which is joined to a streptavidin which is covalently joined to the solid support.

Finally, in still yet another embodiment, this invention provides a method to enrich a nucleic acid sample for previously unknown expressed RNA sequences. The method includes the steps of: i) providing an affinity matrix having at least one oligonucleotide complementary to each known expressed RNA present in a sample; ii) hybridizing RNA from an undifferentiated control cell and differentiated or activated test cell respectively to the affinity matrix thereby removing known expressed RNAs from the control cell and the differentiated or activated test cell; iii) reverse transcribing the RNA from each of the control cell and the differentiated or activated test cell to produce a cDNA, wherein the reverse transcription adds a polymerase chain reaction primer binding region to the cDNAs from the differentiated or activated test cell; iv) combining the cDNAs from the differentiated or activated test cell with the cDNA from the control cell such that there is more cDNA from the control cell than cDNA from the differentiated or activated test cell; v) amplifying the mixture of cDNAs using primers complementary to the primer binding regions such that the amplification results in an enrichment of nucleic acid sequences transcribed in the differentiated or activated test cell at a significantly higher level than in the control cell. In a preferred embodiment, ratio of cDNA from the control cell to cDNA from the test cell, in step (iv) is at least about a 5:1, more preferably at least about 10:1, most preferably at least about 20:1.

Definitions

As used herein, an "oligonucleotide" refers to a single stranded nucleic acid having a length greater than 2 nucleotides, more preferably greater than about 5 nucleotides, and most preferably greater than about 10, 15, 20, or 50 oligonucleotides. The oligonucleotides of this invention can range in length up to about 1000 nucleotides, but preferred lengths range up to a maximum of about 500, more preferably up to about 250 nucleotides, and most preferably up to about 150 nucleotides (bases). An oligonucleotide can include natural (i.e., a, G, C, T or U) or modified bases (i.e., 7-deazaguanosine, inosine, etc.). In addition, the bases in an oligonucleotide can be joined by a linkage other than a phosphodiester bond, so long as it does not interfere with hybridization of the oligonucleotide. Thus, oligonucleotides can be peptide nucleic acids in which one or more of the constituent bases are joined by peptide bonds rather than phosphodiester linkages.

The term nucleic acid "affinity matrix", as used herein, refers to a solid support or gel to which is attached a multiplicity of different oligonucleotides. It is recognized that a nucleic acid template array, itself can act as an affinity matrix. However, in a preferred embodiment, where greater loading (binding) capacity is preferred, the affinity matrix is fabricated using nucleic acids amplified from the template array. Preferred matrix materials do not interfere with subsequent hybridization of attached oligonucleotides. Suitable matrix materials include, but are not limited to paper, glasses, ceramics, metals, metalloids, polacryloylmorpholide, various plastics and plastic copolymers such as Nylon™, Teflon™, polyethylene, polypropylene, poly(4-methylbutene), polystyrene, polystyrene, polystyrene/latex, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and controlled-pore glass (Controlled Pore Glass, Inc., Fairfield, N.J.), aerogels (see, e.g., Ruben et al., *J. Materials Science* 27, 4341–4349 (1992); Rao et al., *J. Material. Science* 28, 3021 (1993); Back et al., *J. Phys. D. Appl. Phys.* 22, 730–734 (1989); Kim & Jang, *J. Am. Ceram. Soc.* 74, 1987–92 (1991) and the like, and other materials generally known to be suitable for use in affinity columns (e.g. HPLC columns).

The term "target nucleic acid" refers to a nucleic acid (often derived from a biological sample), to which the oligonucleotide probe is designed to specifically hybridize. It is the target nucleic acid(s) that the affinity matrices of this invention are designed to capture (bind). The target nucleic acid(s) have sequences that are complementary to the nucleic acid sequence of the oligonucleotide affinity ligand in the affinity matrix. The term target nucleic acid may refer to the specific subsequence of a larger nucleic acid to which oligonucleotide is complementary or to the overall sequence (e.g., gene, cDNA or mRNA) that it is desired to capture. The difference in usage will be apparent from context.

The term "subsequence" refers to a partial sequence of a longer nucleic acid.

The term "affinity ligand" as used herein refers to a molecule present in the affinity matrix that specifically binds to, and thereby captures, a target molecule. Oligonucleotides are preferred affinity ligands in the affinity matrices of this invention.

The terms "nucleic acid template" or "template", as used herein, refer to a nucleic acid that acts as a template for a nucleic acid amplification method. Nucleic acid templates of the present invention serve as templates for the amplification of nucleic acid pools comprising capture probes that are used either in solution or bound to a solid support to provide nucleic acid affinity matrices. Preferred nucleic acid templates additionally include primer binding regions to facilitate amplification. A particularly preferred nucleic acid template comprises a unique sequence (subsequence) that encodes the nucleic acid capture probe, flanked on the 5' and 3' ends by subsequences that act as primer binding regions.

The term "nucleic acid pool" as used herein, refers to a heterogenous collection of nucleic acids. For example, a nucleic acid pool can comprises at least 100, 1000, or 10,000 different nucleic acids. The nucleic acids within a pool often lack an imposed relationship. For example, a pool can be formed from nucleic acids lacking substantial sequence identity with each other (e.g., less than 50% or 75% sequence identity) to each other. Sequence identity is determined between optimally aligned sequences by standard algorithms such as GAP, BESTFIT, FASTA, and TFASTA (Wisconsin Genetics Software Package Release 7.0, Genetics Computer Group, 575 Science Dr., Madison, Wis.). Nucleic acids within the pool typically range in size from 5–100 bases, preferably, 10–50 bases. Typically the nucleic acid pools are prepared by amplification of a heterogenous collection of template nucleic acids (e.g., as found in a template array).

The term "blocking reagent", when used herein in reference to a nucleic acid pool, refers to a pool or solution of one or more nucleic acids that specifically bind to preselected target sequences. The duplexes thus formed are typically incapable of further hybridization.

The term "template array" or "amplification template array" refers to a collection of oligonucleotides that acts as a templates for simultaneous amplification of a collection of nucleic acids. Preferred template arrays are used in the fabrication of affinity ligands for incorporation into an affinity matrix.

The terms "nucleic acid" or "nucleic acid molecule" refer to a deoxyribonucleotide or ribonucleotide polymer in either single-or double-stranded form, and unless otherwise limited, would encompass known analogs of natural nucleotides that can function in a similar manner as naturally occurring nucleotides.

The phrase "nucleic acid message", as used herein refers to a nucleic acid or subsequence thereof that is transcribed when a gene is activated. Thus, nucleic acid messages typically include mRNAs and subsequences thereof. However, nucleic acid messages are used herein to refer to nucleic acids indicative of the presence, absence, or amount of such transcribed sequences. Thus, nucleic acid messages also include nucleic acids derived from such transcripts including, but not limited to cDNA, cRNA, amplification products, and so forth.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence (or about 5° C. lower than the sequence with the highest melting point for a group of sequences) at a defined ionic strength and pH. The $T_m$ is the temperature (under defined ionic strength, pH, and nucleic acid concentration) at which half the duplex molecules (i.e. half the base pairs) are dissociated, or the point where the denaturation rate equals the renaturation rate under given conditions. Typically, stringent conditions will be those in which the salt concentration is less than about 0.01 to 1.0 M Na ion concentration (or other salts) at pH 7.0 to 8.3 and the temperature is at least about 30° C. for short probes (e.g., 16 to 50 nucleotides). Stringent conditions may also be achieved with the addition of destabilizing agents such as formamide.

The term "capture probe", as used herein, refers to a nucleic acid that is complementary to a target nucleic acid. The capture probe, when incorporated into an affinity matrix acts as an affinity ligand that can specifically hybridize to and thereby capture its respective target nucleic acid. It is recognized that capture probes can also exist in solution (e.g. in nucleic acid pools) where they may act as blocking probes or where they can be subsequently bound to a solid support to produce an affinity matrix.

DETAILED DESCRIPTION

Figure 1:
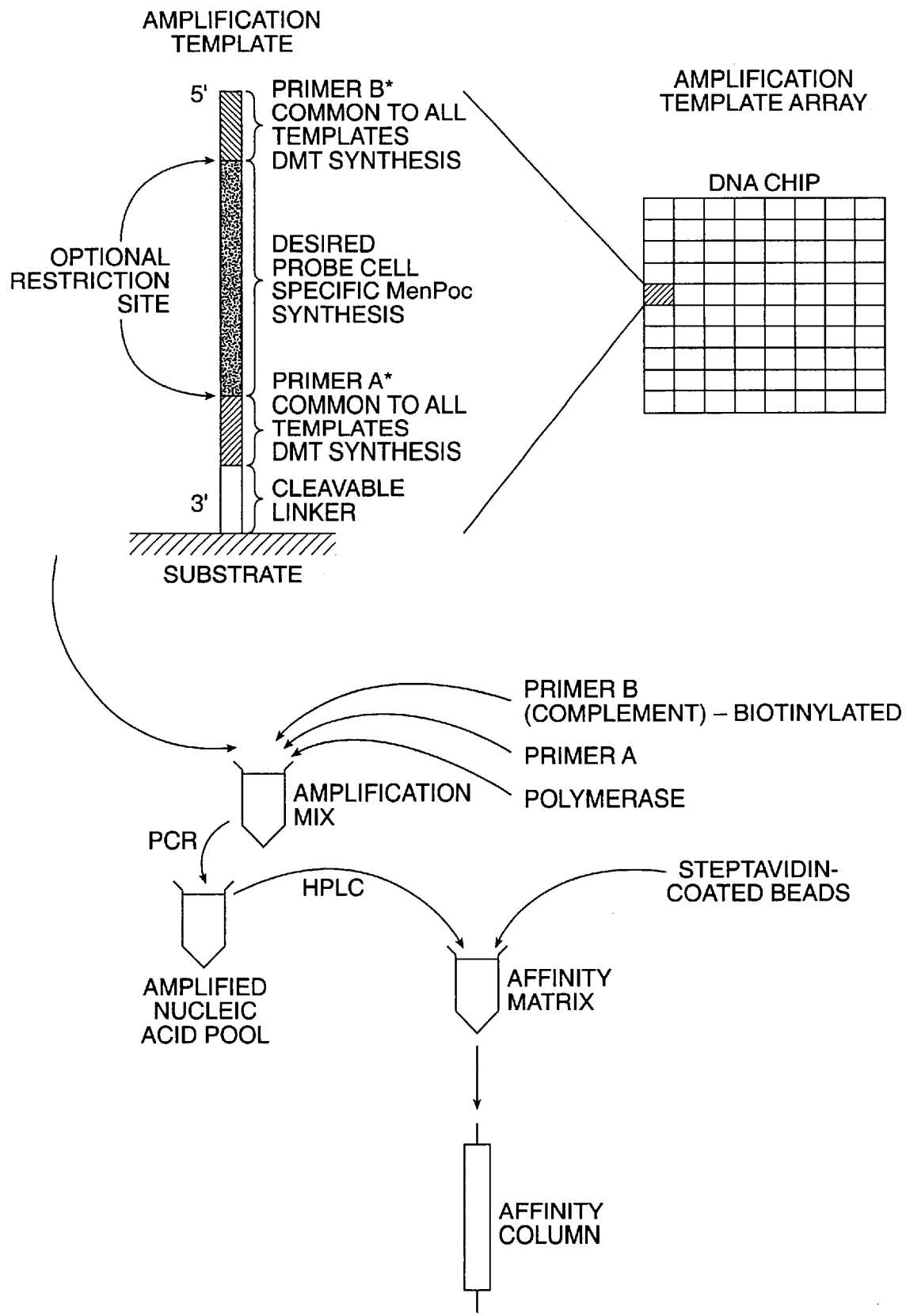
FIG. 1 illustrates a preferred method of making the affinity matrix of this invention. Briefly, a nucleic acid template array bearing a plurality of amplification templates for affinity ligands where each template comprises an affinity ligand (probe) sequence flanked by PCR primer binding sites (primers a and B*) is synthesized (e.g. synthesis using light-directed coupling or mechanically-directed coupling). The affinity templates are amplified via polymerase chain reaction (PCR) using a biotinylated primer. The resulting biotinylated amplification product is then purified via HPLC (e.g. Using a mono Q column, Pharmacia, Piscataway, N.J., USA) and then combined with streptavidin coated beads. The resulting affinity matrix is then packed into a column.

I. Amplified Nucleic Acid Pools and Affinity Matrices.

This invention provides a method of preparing pools of nucleic acids and, by attaching the pool(s) of nucleic acids to a solid support, a method of preparing nucleic acid affinity matrices. Both the pool of nucleic acids and the affinity matrices comprise a number of different preselected nucleic acids that act as affinity ligands. Unlike affinity columns found in the prior art, the nucleic acid pools and affinity matrices of this invention bear a large number of different preselected nucleic acid affinity ligands. The nucleic acid pools and affinity matrices of this invention can thus be used to simultaneously bind to and capture a large number of different nucleic acids and thereby provide a sample with either reduced representation of those nucleic acids or conversely, where the selected nucleic acids are retrieved, a sample enriched for the selected collection of nucleic acids. Both the amplified pools of nucleic acids and the affinity matrices of this invention have a large number of uses which are discussed below.

A) Amplified Nucleic Acid Pools.

The nucleic acid pools of this invention are particularly useful when used as a blocking reagents (blocking probes). A blocking reagent is a reagent that reduces or prevents the hybridization of one or more nucleic acids to particular components of a sample. For example, where it is desired to detect a particular (target) nucleic acid that is expressed at low levels in a nucleic acid sample, selective elimination of other nucleic acids that are present at high levels in the sample can improve detection and isolation of the target sequence. In this case, a nucleic acid pool containing nucleic acids complementary to the nucleic acids it is desired to block in the sample can be hybridized to the sample. The nucleic acid pool (blocking reagent) will hybridize to complementary sequences in the sample, form stable hybrid duplexes, and thereby prevent interaction (e.g., nonspecific binding) of the blocked nucleic acids with the capture sequence. Thus, for example, where gene products, such as actin or GADPH, are typically overexpressed in a nucleic acid sample, the nucleic acid pool will be prepared containing nucleic acids complementary to those (e.g., actin and GADPH) RNAs. When the blocking reagent is combined (hybridized) to the sample, the GADPH and actin RNAs will hybridize with the blocking reagent and their participation in other reactions will be reduced or eliminated.

In another embodiment, the nucleic acid pools can be used to provide control nucleic acid mixtures for use as test standards for evaluation and quality control of various nucleic acid detection and/or isolation methods. Nucleic acid pools can be prepared containing nucleic acids that differ from each other in only one, two, three, or more particular nucleotides. The nucleic acid pool can then be used as a standard sample for evaluating the ability of a method (e.g. a particular HPLC column) to isolate and/or distinguish between the various nucleic acid components of the pool. In this way the ability of a device or method to detect, isolate, and/or discriminate particular nucleic acids from a pool of closely related nucleic acids can be evaluated.

B) Affinity Matrices.

The affinity matrices of this invention are also useful in a wide variety of contexts. For example, where it is desired to analyze mRNA expression levels of particular genes in a complex nucleic acid sample (e.g., total mRNA) (see, e.g., PCT/US97/01603, filed Jan. 22, 1997, incorporated by reference in its entirety for all purposes) it is often desirable to eliminate nucleic acids produced by genes that are constitutively overexpressed and thereby tend to mask gene products expressed at characteristically lower levels. Thus, in one embodiment, the affinity matrix can be used to remove a number of preselected gene products (e.g., actin, GAPDH, etc.). This is accomplished by providing an affinity matrix bearing nucleic acid affinity ligands complementary to the gene products (e.g., mRNAs or nucleic acids derived therefrom) or to subsequences thereof. Hybridization of the nucleic acid sample to the affinity matrix will result in duplex formation between the affinity ligands and their target nucleic acids. Upon elution of the sample from the affinity matrix, the matrix will retain the duplexes nucleic acids leaving a sample depleted of the overexpressed target nucleic acids.

The affinity matrix can also be used to identify unknown mRNAs or cDNAs in a sample. Where the affinity matrix contains nucleic acids complementary to every known gene (e.g., in a cDNA library, DNA reverse transcribed from an mRNA, mRNA used directly or amplified, or polymerized from a DNA template) in a sample, capture of the known nucleic acids by the affinity matrix leaves a sample enriched for those nucleic acid sequences that are unknown. In effect, the affinity matrix is used to perform a subtractive hybridization to isolate unknown nucleic acid sequences. The remaining "unknown" sequences can then be purified and sequenced according to standard methods.

The affinity matrix can also be used to capture (isolate) and thereby purify unknown nucleic acid sequences. For example, an affinity matrix can be prepared that contains nucleic acid (affinity ligands) that are complementary to sequences not previously identified, or not previously known to be expressed in a particular nucleic acid sample. The sample is then hybridized to the affinity matrix and those sequences that are retained on the affinity matrix are "unknown" nucleic acids. The retained nucleic acids can be eluted from the matrix (e.g. at increased temperature, increased destabilizing agent concentration, or decreased salt) and the nucleic acids can then be sequenced according to standard methods.

Similarly, the affinity matrix can be used to efficiently capture (isolate) a number of known nucleic acid sequences. Again, the matrix is prepared bearing nucleic acids complementary to those nucleic acids it is desired to isolate. The sample is contacted to the matrix under conditions where the complementary nucleic acid sequences hybridize to the affinity ligands in the matrix. The non-hybridized material is washed off the matrix leaving the desired sequences bound. The hybrid duplexes are then denatured providing a pool of the isolated nucleic acids. The different nucleic acids in the pool can be subsequently separated according to standard methods (e.g. gel electrophoresis).

As indicated above the affinity matrices can be used to selectively remove nucleic acids from virtually any sample containing nucleic acids (e.g., in a cDNA library, DNA reverse transcribed from an mRNA, mRNA used directly or amplified, or polymerized from a DNA template, and so forth). The nucleic acids adhering to the column can be removed by washing with a low salt concentration buffer, a buffer containing a destabilizing agent such as formamide, or by elevating the column temperature.

In one particularly preferred embodiment, the affinity matrix can be used in a method to enrich a sample for unknown RNA sequences (e.g. expressed sequence tags (ESTs)). The method involves first providing an affinity matrix bearing a library of oligonucleotide probes specific to known RNA (e.g., EST) sequences. Then, RNA from undifferentiated and/or unactivated cells and RNA from differentiated or activated or pathological (e.g., transformed) or otherwise having a different metabolic state are separately hybridized against the affinity matrices to provide two pools of RNAs lacking the known RNA sequences.

The RNAs from the differentiated (or activated, etc.) cells are reverse transcribed to produce cDNAs bearing cleavable PCR priming regions. (See, e.g., Van Gelder, et al., *Proc. Natl. Acad. Sci. USA*, 87: 1663–1667 (1990) and Eberwine et al. *Proc. Natl. Acad. Sci. USA*, 89: 3010–3014). Similarly, the RNAs from the undifferentiated cells are reverse transcribed to make cDNAs without PCR priming sites. The two resulting pools of cDNAs are then combined with the cDNAs from the undifferentiated cells in great excess (e.g. at least 10 fold excess). At this high concentration, during PCR the cDNAs from the undifferentiated cells will hybridize with complementary sequences from the differentiated cells and form stable duplexes thereby preventing amplification of the corresponding sequences. Conversely, those nucleic acids unique to the differentiated cells are differentially amplified. Thus, the PCR effectively performs a subtractive hybridization resulting in a nucleic acid sample enriched for unknown ESTs that are characteristic of the activated or differentiated state.

II. Preparation of the Affinity Matrix.

Methods of preparation of the affinity matrices of this invention are illustrated in FIG. 1. The methods generally involve first identifying the nucleic acids (capture probes) it is desired to include in the affinity matrix. Once the capture probes have been identified, corresponding nucleic acid templates can be designed from which the capture probes can be amplified. The nucleic acid templates are all attached to a solid support thereby forming a "template array" (see FIG. 1, "DNA chip"). In a preferred embodiment, each template nucleic acid is located in a particular preselected region on the solid support. Thus, for example, the DNA chip of FIG. 1 shows an array of "rectangles" where each rectangle contains a different template nucleic acid.

The template nucleic acids are amplified en mass (e.g., via PCR) to produce a population of different nucleic acids (see FIG. 1). The number of molecules of each species of nucleic acid in the population will be substantially greater than the number of template molecules used to amplify that species. The amplified nucleic acids are then attached to a solid support (e.g. glass or plastic beads) to form an affinity matrix. The affinity matrix can be arranged or packaged into a variety of forms. In one preferred affinity matrix the matrix material is glass beads having attached capture probes and the beads are packed into a column to thereby produce an affinity column (see FIG. 1).

The method of preparation of affinity matrices can be generally summarized in the following steps:

1) Nucleic acids (capture probes) to be included in the affinity matrix are identified;
2) A template array is provided that bears a plurality of different nucleic acids where each different nucleic acid is capable of acting as an amplification template to amplify one of the capture probes;
3) The nucleic acid templates in the template array are amplified to provide a population of capture probes where the number of molecules of each capture probe is substantially greater than the number of corresponding template molecules from which the capture probe species was amplified; and
4) The capture probes are then attached to a solid support (matrix material) to thereby produce an affinity matrix.

Each of these steps is discussed in detail below.

1) Identification/Selection of Nucleic Acids to Include in the Affinity Matrix.

As indicated above, the first step in the claimed method of preparing either a free solution containing a multiplicity of preselected oligonucleotides or an affinity matrix of this invention involves determining which oligonucleotides to include in the solution or matrix. Once the desired oligonucleotides are identified, an amplification template for each oligonucleotide is designed and the collection of amplification templates form an amplification template array.

One of skill in the art will appreciate that amplification templates can have either the same nucleotide sequence as the desired amplified oligonucleotides or can be complementary to those oligonucleotides. The sense of the dominant amplified strand can be controlled by using unequal amounts of primer so that the primer for the undesired strand is effectively rate limiting during the amplification step. Methods of determining appropriate template sense and primer ratios are well known to those of skill in the art (see, e.g., *PCR Protocols: a Guide to Methods and Applications*, Innis et al., eds. Academic Press, Inc. N.Y. 1990). For convenience, when discussing template construction, template sequences capable of amplifying the desired oligonucleotides (capture probes) are discussed as though they have the same sequence as the amplified product, recognizing that the actual corresponding template sequence can be the same or complementary to the ultimate amplified product.

In addition to the template sequence encoding the capture probe, the template nucleic acid can include additional (ancillary) sequences to facilitate amplification and purification of the capture probe. Thus, the design of nucleic acid templates can involve both the selection of the capture probe component of the template and the design and inclusion of ancillary sequences. Each of these components is described separately below.

a) Identification/Selection of Capture Probe Component of Amplification Template.

i) Arbitrary Preselected Oligonucleotides.

One of skill in the art will appreciate that virtually any oligonucleotide can be included in the affinity matrix. In a preferred embodiment, however, oligonucleotides are selected that are complementary to a sequence or subsequence of the nucleic acid(s) it is desired to bind to the affinity matrix. In addition, capture oligonucleotide sequences are selected to minimize self complementarity which may result in hairpin formation, or other secondary structure that may interfere with hybridization. In addition, the oligonucleotides can incorporate various base substitutions to reduce secondary structure (e.g. inosine, 7-deazaguanosine, etc.).

In one embodiment, the oligonucleotide affinity ligands are selected to bind and thus remove nucleic acids (e.g. mRNAs) that are characteristically overexpressed and thus tend to mask the expression of other nucleic acids that are typically expressed at lower levels. Such overexpressed nucleic acids include, but are not limited to, the common "housekeeping" genes such as actin, GAPDH, and other well known constitutively expressed genes.

In another embodiment, the affinity matrix oligonucleotides are selected to hybridize to one or more target nucleic acids it is desired to purify from a sample of biological molecules. Thus, for example, where it is desired to isolate a particular set of nucleic acids from a biological sample, the affinity matrix is provided containing oligonucleotides complementary to sequences or subsequences of the nucleic acids it is desired to isolate.

ii) Selecting Oligonucleotide Probes to Bind All Known Sequences.

In still yet another embodiment, the affinity matrix nucleic acids can be selected to bind to, and thus remove, substantially every known mRNA, cDNA, expressed sequence tag (EST), or other known nucleic acid in a sample, and thus provide a nucleic acid sample enriched for unknown sequences. In a preferred embodiment, oligonucleotide "probes" designed for such a selection are chosen to have a relatively uniform melting point ($T_m$). The probes are also preferably selected to have a low probability of hybridizing to an unknown message and thus have a $T_m$ above a characteristic threshold which is the melting point of the most similar non-selected nucleic acids expected to be in the sample.

A probe selection process embodying the above-identified criteria can be formalized in the following steps:

1) An allowable $T_m$ interval for the probes is selected.
2) A $T_m$ threshold is selected.
3) For each known nucleic acid sequence that is to be captured by the affinity matrix the following steps are performed:
   a) All oligonucleotide probes of a preselected length complementary to the sequence and whose $T_m$ falls within the allowable $T_m$ interval are determined.
   b) The likelihood of each oligonucleotide probe being present in an unknown message is calculated;
   c) The oligonucleotide probes are then sorted by likelihood with the least likely probe listed first; and finally
   d) The first probe in the list whose $T_m$ to all other known messages in the sample is below the mismatch $T_m$ is selected for inclusion in the affinity matrix.

As indicated above, the allowable $T_m$ interval is arbitrary and chosen largely for convenience. Of course, one of skill will appreciate that a narrower $T_m$ will produce fewer suitable probes, while a broader $T_m$ will make optimization of amplification and hybridization conditions more difficult. Similarly, a suitable mismatch $T_m$ is also arbitrary. Of course, the mismatch $T_m$ must be lower than the $T_m$ interval otherwise the probes comprising the affinity matrix will be unable to specifically discriminate between target nucleic acids and non-target nucleic acids having similar, but not identical, sequences.

The allowable $T_m$ interval (i.e. the $T_m$ of the selected probes their complementary sequences) typically spans a maximum range of about 30° C., preferably a maximum range of about 20° C., more preferably a maximum range of about 10° C. and most preferably a maximum range of about 5° C. Allowable $T_m$ intervals range from about 30° C. to about 80° C., more preferably from about 35° C. to about 70° C., more preferably from about 40° C. to about 60° C., and most preferably about 45° C. to about 55° C. As indicated above, the mismatch $T_m$ is lower than the low side of the allowable $T_m$ interval, typically at least about 5° C. lower, preferably at least about 10° C. lower, more preferably at least about 15° C. lower and most preferably at least about 20° C. lower than the allowable $T_m$ interval.

As indicated below (in section (2)) above, the oligonucleotides can have a preselected length ranging from 2 up to about 1000 nucleotides, more preferably from about 6 to about 150 nucleotides, most preferably from about 6 to about 50 nucleotides.

Methods of calculating thermal melting points ($T_m$) of two nucleic acids (e.g. an oligonucleotide and its complement) are well known to those of skill in the art. Detailed calculations are provided for example in Chapter 2 of *Laboratory Techniques in Biochemistry and Molecular Biology, Vol. 24: Hybridization With Nucleic Acid Probes*, P. Tijssen, ed. Elsevier, N.Y., (1993)). (See, also Sambrook, et al., *Molecular Cloning: a Laboratory Manual*, 2nd Ed., Vols. 1–3, Cold Spring Harbor Laboratory (1989)), *Methods in Enzymology, Vol. 152: Guide to Molecular Cloning Techniques*, Berger and Kimmel, eds., San Diego: Academic Press, Inc. (1987), or *Current Protocols in Molecular Biology*, Ausubel, et al. eds., Greene Publishing and Wiley-Interscience, New York (1987)).

In general, the likelihood of an oligonucleotide probe being present in an unknown message is determined by calculating a nucleic acid probability distribution for the particular genome(s) or nucleic acid collection(s) of interest. The probability (likelihood) of occurrence of the oligonucleotide probe in that distribution is then determined.

For example, a simple distribution representing the human genome is the frequency of occurrence of each of the bases; a, C, G and T in the human genome. Since the human genome is not yet fully sequenced, the complete frequency distribution can be estimated by extrapolation from a sample distribution. Thus, for example, the base composition of the human genome can be estimated by selecting all of the human genome sequences listed in GenBank. The total number of each nucleotide a, G, C, and T given as $N_A$, $N_C$, $N_G$, and $N_T$, respectively can then be easily totaled. The probability of each nucleic acid (p(X) where x is a, G, C, or T) can then be determined as:

$$p(X) = \frac{N_X}{N_A + N_C + N_G + N_T}$$

The likelihood of an oligonucleotide O of length Y where the oligonucleotide is represented as $$O=X_1-X_2-X_3 \ldots -X_y$$

where $X_1$ is the nucleotide at position 1, $X_2$ is the nucleotide at position 2, and so forth, occurring in the given distribution is then calculated as $$p(O)=p(X_1)p(X_2)p(X_3) \ldots p(X_y)$$

In a nucleic acid population where the frequency of occurrence of a, G, C and T is 0.3, 0.3, 0.2 and 0.2, respectively, the probability (p(O)) of an oligonucleotide having the sequence AAGATT is $$p(O) = p(A)p(A)p(G)p(A)p(T)p(T)$$
$$= (0.3)(0.3)(0.3)(0.3)(0.2)(0.2)$$
$$= 0.000324$$

Such a distribution of course reflects only base composition and lacks sequence information. A probability distribution incorporating sequence information can be generated by calculating the marginal probability distribution for a particular base given a certain combination of preceding bases.

Thus, for example, the probability distribution of each dinucleotide can be calculated as follows:

$$p(AA|XA) = \frac{N_{AA}}{N_{AA} + N_{GA} + N_{CA} + N_{TA}}$$

where p(AA|XA) is the probability of occurrence of the dinucleotide AA given a preceding a, and $N_{AA}$, $N_{GA}$, $N_{CA}$ and $N_{TA}$ are the numbers of occurrence of the dinucleotides AA, GA, CA and TA, respectively. Similarly, the probability of occurrence of the dinucleotide AT given a preceding C is calculated as:

$$p(AT|XC) = \frac{N_{AT}}{N_{AC} + N_{GC} + N_{CC} + N_{TC}}$$

where $N_{AC}$, $N_{GC}$, $N_{CC}$ and $N_{TC}$ are the numbers of occurrence of the dinucleotides AC, GC, CC and TC, respectively. Other dinucleotide probabilities can be determined in the same manner.

The likelihood of an oligonucleotide occurring in the distribution is then calculated as the product of the marginal probability (frequency of occurrence) of its respective dinucleotides given the preceding base. Thus, for example the likelihood of oligonucleotide O occurring in the distribution where O is ACGTTACC is $$p(O)=p(AC|XC)p(CG|XG)p(GT|XT)p(TT|XT)p(TA|XA)p(AC|XC)p(CC|XC)p(C)$$

One of skill will readily appreciate that similar distributions can be calculated for trinucleotides, tetranucleotides and so forth to any arbitrary length. Each higher order distribution incorporates progressively more sequence information. The likelihood of a particular oligonucleotide existing in such a distribution can be calculated as illustrated.

The selection of the particular oligonucleotide frequency distribution used to calculate probe likelihoods is essentially arbitrary. As indicated above, to a certain extent, higher order distributions capture more sequence information. The ability of a particular order probability distribution to accurately reflect likelihood of occurrence of an oligonucleotide in a nucleic acid sample, can be determined by comparing predicted likelihood values for various oligonucleotides with the actual frequency of occurrence of those oligonucleotides in a sample nucleic acid data set. The closer the predicted likelihood approximates the actual likelihood, the better is the probability distribution.

Such a comparison can be made, for example, by dividing a collection of sequences (e.g. the GenBank listing of human cDNAs) in half and using the first half to calculate a nucleic acid frequency distribution and predict the likelihood of occurrence of particular oligonucleotides in the second half of the collection. The predicted values can then be compared with the actual frequency of occurrence of the oligonucleotides in the second half of the sequence set and the accuracy of the prediction determined.

iii) Selecting Oligonucleotide Probes to Bind Unknown Sequences.

The method described above provides a means of selecting probes expected to bind to substantially all known sequences in a given nucleic acid sample. Conversely, it is possible to select oligonucleotide probes expected to bind to N unknown nucleic acids in a sample, where N is the number of oligonucleotide probes to be selected. The selection method basically involves creating a list of all possible probes of a given length, deleting from the list probes that hybridize to known messages, and then selecting the N number of probes that have the greatest likelihood of occurring in an unknown message. The method can be formalized as follows:

1) A list ($L_1$) of possible oligonucleotide probes (preferably all probes) of length K is calculated;
2) Oligonucleotide probes from list $L_1$ that hybridize to known messages (or messages of interest) are deleted from the list.
3) The probability of occurrence of each of the oligonucleotide probes of list $L_1$ in a nucleic acid probability distribution is calculated;
4) The following steps are repeated until N probes are identified:
   a) The list ($L_1$) is sorted from the highest probability to the lowest.
   b) The highest probability probe is added to list of selected probes, $L_2$.

Step (4) can additionally include recalculating the probabilities on the condition that the probability distribution contains no nucleic acids complementary to those oligonucleotides already selected.

The list of all possible probes of length K can be calculated in a simple combinatorial manner. Thus there are 4 probes of length 1 (A, C, G, T), 16 probes of length 2 (AA, AC, AG, AT, CA, CC . . . , TA, TC, TG, TT) and so forth. The distribution of message sequences can be calculated as described above as can the likelihood of occurrence of each probe in $L_1$ occurring in the distribution. As indicated above, K most preferably ranges from about 6 to about 50 nucleotides.

The probability distribution and likelihood is calculated as described above. The recalculation conditioned on the fact that no selected probe ($L_2$) is a complementary to an unknown is accomplished again, as described above.

The limitations on thermal melting point can also be imposed on selected probes. Thus, only probes having a $T_m$ above a critical threshold and/or probes having a $T_m$ within a specific allowable interval can be selected for inclusion in the affinity matrix.

Either of the above-described probe selection methods can include the additional condition that the $T_m$ of and by one of the selected probes to the other selected probes must be below the mismatch $T_m$. This will prevent cross hybridization between probes comprising the affinity matrix.

While the methods described above use nucleic acid samples (e.g. sequences selected from a genetic database such as GenBank) to predict the nucleic acid frequency distribution of a "population" (e.g. the entire genome of a particular species), one of skill will appreciate that where a particular genome is fully sequenced there is no need to calculate the likelihood of occurrence of particular probes. Those nucleic acid sequences that it is desired to capture with the affinity matrix can be expressly included.

B) Ancillary Sequences to Facilitate Amplification/Purification.

As indicated above, the template nucleic acids forming the template array are used as templates for a nucleic acid amplification step (step 3 of the method described above). In addition to the nucleic acid sequence (or subsequence) encoding the affinity ligands (capture probes) that are to be included in the affinity matrix, the nucleic acid template(s) can additionally include ancillary sequences that facilitate amplification and/or purification.

For example, polymerase based amplification systems typically require a double-stranded priming region for binding and initiation of the polymerase. The double stranded priming region is typically provided by including, in the amplification reaction mixture, primers that are complementary to a portion of the template that is to be amplified. The primers bind to the template (at primer binding regions which are complementary to the primers) forming a double stranded region in to which the polymerase binds and initiates transcription.

While primers can be selected that specifically hybridize to each of the template nucleic acids such an approach may require a large number of different primers. Thus, in a preferred embodiment, the template nucleic acids additionally include terminal subsequences (primer binding sequences) that are common to all of the template nucleic acids. All of the constituent nucleic acids can then be amplified with a single set of primers and one set of reaction conditions.

Thus, particularly preferred template nucleic acids comprise, in order, a common first priming domain, a "unique" domain that encodes the affinity ligand (capture probe), and a second common priming domain (illustrated in FIG. 1, as Primer a* binding region, specific affinity ligand, and Primer B* binding region, respectively). The first and second priming domains can be identical thereby allowing the use of a single primer, or alternatively, the priming domains may have different sequences and thus require two primers for amplification. Priming domains can range in length from about 4 to about 50 nucleic acids, preferably from about 4 to about 40 nucleic acids, more preferably from about 4 to about 30 nucleic acids, and most preferably from about 4 to about 20 nucleic acids. Particularly preferred priming domains can range from about 6 to about 15 or about 20 nucleic acids in length. Priming domains are preferably selected so that the priming domain does not also form a subsequence in any of the unique regions of the templates.

Where it is desired to remove the amplification priming domain from the amplification product, the primer domain can additionally incorporate a nucleic acid sequence that is recognized by a restriction endonuclease. Thus, for example, a six nucleotide priming sequence can include a four base recognition site which when cleaved by a four base cutter leaves a two base tail. Longer nucleotide priming sequences can provide longer recognition sites (e.g. 5, 6, 7, . . . 10). One of skill will readily appreciate that offset sites can be used allowing a clean cut end. Recognition sites and restriction endonucleases are well known to those of skill in the art and selection of particular recognition domains and their corresponding restriction enzyme are well known to those of skill in the art. (See, e.g. Gibco BRL, Grand Island, N.Y., USA, or New England Biolabs, Beverly, Mass., USA for a list of restriction nucleases and their recognition sites.)

On occasion, it will be desirable to purify one or more of the nucleic acids amplified from the nucleic acid template array. Such purification can be facilitated by incorporating specific (predetermined) nucleic acid "recognition" sequences into the nucleic acid template(s) of the nucleic acid sequences it is desired to purify. These nucleic acids can then be isolated from the pool of amplified nucleic acids by use of a nucleic acid affinity column with capture probes complementary to the recognition sequences. Thus, for example, the template(s) can include a poly A tail which will facilitate purification of the amplification product using an oligo dT column. Other recognition sequences are, of course, suitable as well. Generally a recognition sequence will be selected such that it exists only in the amplified nucleic acids it is desired to purify.

2) Preparation of a Template Array.

While the nucleic acid templates can be provided free in solution, in a preferred embodiment the templates are themselves bound to a solid support forming an amplification template array. In a particularly preferred embodiment, the amplification template arrays of this invention are high density oligonucleotide arrays comprising at least about 50, generally at least about 100, more generally at least about 500, most generally at least about 1000, preferably at least about 5,000, more preferably at least about 10,000, most preferably at least about 50,000, 100,000, 500,000 or even at least about 1,000,000 different nucleic acid probes. Such high density arrays comprise a probe density of generally greater than about 60, more generally greater than about 100, most generally greater than about 600, often greater than about 1000, more often greater than about 5,000, most often greater than about 10,000, preferably greater than about 40,000 more preferably greater than about 100,000, and most preferably greater than about 400,000 different oligonucleotide probes per $cm^2$. The capture probes incorporated into the affinity matrix, and hence the component of the nucleic acid template(s) encoding the affinity ligand (capture probe) itself can range in length from about 2 nucleotides acids up to about 1000 nucleotides acids, generally from about 5 to about 500 nucleotides acids, more generally from about 10 to about 150 nucleotides acids, most generally from about 10 to about 100 nucleotides acids, preferably from about 10 to about 75 nucleotides acids, more preferably from about 10 to about 50 nucleotides, and most preferably from about 15 to about 40 nucleotides in length. Where the template nucleic acids include ancillary sequences, as discussed above, the template sequence lengths will be increased accordingly.

Although a planar array surface is preferred, the array may be fabricated on a surface of virtually any shape or even a multiplicity of surfaces. Methods of making such amplification template arrays are discussed below.

A) Combinatorial Chemistry

As indicated above, the nucleic acids acting as "capture" probes in the affinity matrices of this invention are preferably amplified from a multiplicity of amplification templates, more preferably from a group of templates that comprising a high density array of oligonucleotides. Methods of forming high density arrays of oligonucleotides, peptides and other polymer sequences with a minimal number of synthetic steps are known. The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 which disclose methods of forming vast arrays of peptides, oligonucleotides and other molecules using, for example, light-directed synthesis techniques, which are incorporated herein by reference. See also, Fodor et al., *Science*, 251, 767–77 (1991) which is incorporated herein by reference. These procedures for synthesis of polymer arrays are now referred to as VLSIPS™ procedures. Using the VLSIPS™ approach, one heterogenous array of polymers is converted, through simultaneous coupling at a number of reaction sites, into a different heterogenous array. See, U.S. application Ser. No. 07/796,243 (now U.S. Pat. No. 5,384,261) and Ser. No. 07/980,523 (now U.S. Pat. No. 5,677,195) which are incorporated herein by reference.

The development of VLSIPS™ technology as described in the above-noted U.S. Pat. No. 5,143,854 and PCT patent publication Nos. WO 90/15070 and 92/10092, is considered pioneering technology in the fields of combinatorial synthesis and screening of combinatorial libraries. More recently, patent application Ser. No. 08/082,937 (now abandoned), filed Jun. 25, 1993 (and incorporated herein by reference) describes methods for making arrays of oligonucleotide probes that can be used to check or determine a partial or complete sequence of a target nucleic acid and to detect the presence of a nucleic acid containing a specific oligonucleotide sequence.

In brief, the light-directed combinatorial synthesis of oligonucleotide arrays on a glass or other surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithogaphic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform the synthetic steps, since the monomers do not attach to one another via a phosphate linkage. Instead, peptide synthetic methods are substituted. See, e.g., Pirrung et al. U.S. Pat. No. 5,143,854 which is incorporated herein by reference.

Peptide nucleic acids are commercially available from, e.g., Biosearch, Inc. (Bedford, Mass.) which comprise a polyamide backbone and the bases found in naturally occurring nucleosides. Peptide nucleic acids are capable of binding to nucleic acids with high specificity, and are considered "oligonucleotide analogues" for purposes of this disclosure.

In addition to the foregoing, additional methods which can be used to generate an array of oligonucleotides on a single substrate are described in co-pending applications Ser. No. 07/980,523, filed Nov. 20, 1992, and Ser. No. 07/796,243, filed Nov. 22, 1991 and in PCT Publication No. WO 93/09668, which are incorporated herein by reference. In the methods disclosed in these applications, reagents are delivered to the substrate by either (1) flowing within a channel defined on predefined regions or (2) "spotting" on predefined regions. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "a" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer a flows through or is placed in all or some of the channel(s). The channels provide fluid contact to the first selected regions, thereby binding the monomer a on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer a can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

The "spotting" methods of preparing compounds and libraries of the present invention can be implemented in much the same manner as the flow channel methods. For example, a monomer a can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette to deliver the monomer solution to the substrate and a robotic system to control the position of the micropipette with respect to the substrate. In other embodiments, the dispenser includes a series of tubes, a manifold, an array of pipettes, or the like so that various reagents can be delivered to the reaction regions simultaneously.

B) Combined Synthetic Methods.

Using the light-directed coupling and mechanically-directed coupling methods described above, one can readily synthesize high density amplification template arrays. However, where all of the template nucleic acids include common sequences (e.g. the primer binding regions) the high density amplification template arrays can be produced using combined (hybrid) synthesis methods. Combined methods utilize standard chemistry (e.g. DMT protected phosphoramidite chemistry) for the synthesis of the common regions of the templates and light-directed or mechanically-directed methods for the specific binding (affinity ligand) regions of the templates. Thus, for example, the first primer binding regions can be synthesized on the solid support according to any standard oligonucleotide synthesis method (e.g. standard phosphotriester chemistry). The final base added can bear a MenPoc or an Fmoc protecting group allowing the "unique" (affinity ligand) region to be synthesized as described above using any of the light-directed or mechanically-directed coupling methods. The last nucleotide added to the "unique" region preferably bears a terminal dimethoxytrityl (DMT) protecting group thereby allowing the second primer binding region to be synthesized using standard oligonucleotide synthesis chemistry.

While any oligonucleotide synthesis method, including solid and liquid phase, phosphite-triester and phosphotriester chemistries, is suitable, oligonucleotide synthesis is preferably carried in solid phase using the solid phase phosphoramidite triester method described by Beaucage et. al., *Tetrahedron Letts.* 22 (20): 1859–1862 (1981). The synthesis can be performed manually or using an automated oligonucleotide synthesizer (see, e.g. Needham-VanDevanter et al. *Nucleic Acids Res.* 12:6159–6168 (1984)). Methods of oligonucleotide synthesis are routine and well known to those of skill in the art. (See, e.g. Itakura, U.S. Pat. No. 4,401,796; Caruthers et al., U.S. Pat. Nos. 4,458,066 and 4,500,707; Beaucage et al., *Tetrahedron Lett.,* 22: 1859–1862 (1981); Matteucci et al., *J. Amer. Chem. Soc.,* 103: 3185–3191 (1981); Caruthers et al., *Genetic Engineering,* 4: 1–17 (1982); Jones, chapter 2, Atkinson et al., chapter 3, and Sproat et al., chapter 4, in Gait, ed. *Oligonucleotide Synthesis: a Practical Approach,* IRL Press, Washington D.C. (1984); Froehler et al., *Tetrahedron Lett.,* 27: 469–472 (1986); Froehler et al., *Nucleic Acids Res.,* 14: 5399–5407 (1986); Sinha et al. *Tetrahedron Lett.,* 24: 5843–5846 (1983); and Sinha et al., *Nucl. Acids Res.,* 12: 4539–4557 (1984).

One of skill in the art will appreciate that where different synthesis are to be combined for template synthesis, different protecting groups should also be incorporated. Thus, for example, where the first primer binding domain is synthesized using a phosphotriester chemistry, the 5' hydroxyl group is preferably protected with a dimethoxytrityl (DMT) group. The last nucleotide coupled however, is preferably protected with a protecting group compatible with the light-directed or mechanically-directed synthesis methods (e.g. a Fmoc, Tboc, or MenPoc) with a MenPoc group being most preferred for compatibility with light-directed coupling methods. Then the last nucleotide of the unique region added using light-directed synthesis methods will be protected with a DMT group (or other group compatible with the new synthesis chemistry) thereby facilitating synthesis of the second primer binding region using phosphotriester chemistry again.

The common primer binding regions of the template oligonucleotides can be synthesized de novo as described above using the light-directed, mechanically directed or hybrid synthesis methods. Alternatively, the complete primer binding regions can be synthesized in a batch process and the completed primer binding region sequence can then be coupled to the solid support forming the amplification template array or to the unique (affinity ligand) region of the templates present in the template array. Synthesis according to this approach thus involves coupling the first primer binding region to the substrate of the amplification template array (either directly or through a linker). The primer binding region can be provided with a terminal protecting group, or one can be added afterwards. The unique region is then synthesized using light-directed or mechanically-directed coupling methods. Finally the second complete primer binding region is covalently linked to the terminus of the unique region. Coupling of oligonucleotides simply involves linking the 3' hydroxyl of one oligonucleotide with the 5' hydroxyl of a second oligonucleotide (or to an activated site on a solid support or linker). The linkage can be through the formation of a phosphodiester linkage. Typically this is accomplished by providing one of the oligonucleotides with an activated or activatable terminal phosphate. Methods of providing such phosphate groups and linking oligonucleotides are well known to those of skill in the art. (See, e.g., WO 85/01051 and WO/90/03382 which are incorporated herein by reference).

Both the above-described combinatorial synthetic methods as well as the standard synthetic methods result in the production of oligonucleotides linked to a solid support (e.g. a glass slide or controlled pore glass) via a linker. Typically in these methods oligonucleotide synthesis commences by coupling of a nucleotide to a reactive group on a linker which in turn is bound to the solid support. The reactive group can be a terminal hydroxyl directly on the solid support, or the 3' or 5' hydroxyl of a nucleotide which in turn is bound to the solid support either directly or through a linker. Suitable linkers are well known to those of skill in the art. (see, e.g. Gait, et al. ed. *Oligonucleotide Synthesis: a Practical Approach*, IRL Press, Washington D.C. (1984); U.S. Pat. No. 5,143,854; PCT Application No. WO 90/15070; Fodor et al., PCT Publication Nos. WO 92/10092 and WO 93/09668, and copending U.S. Ser. No. 08/431,196 (now U.S. Pat. No. 5,624,711) filed on Apr. 27, 1995; and 08/374,492 (now U.S. Pat. No. 5,679,773), filed on Jan. 17, 1995).

Where it is desired to perform the subsequent amplification with the template nucleic acids in solution phase, the linkers can be cleaved according to standard methods (e.g. treatment with concentrated ammonia). Conversely, where the subsequent amplifications are to be performed with the template nucleic acids attached to a solid support, the linker is not cleaved before amplification. In a preferred embodiment, the amplification is performed with the template oligonucleotides retained on the solid support. The amplification template array can then be reused as a template for a number of amplifications and the production of a large number of affinity matrixes.

3) Amplification of the Nucleic Acid Templates to Provide a Population of Capture probes.

a) Amplification.

The affinity matrices of this invention comprise at least about 50, preferably at least about 100, more preferably at least about 500, 1000, 5,000, 10,000, 50,000, 100,000, 500,000 and even at least about 1,000,000 different nucleic acid probes. One of skill in the art will appreciate that the chemical synthesis of each nucleic acid individually in quantities sufficient to provide an affinity matrix with sufficient loading capacity to isolate useful quantities of target nucleic acids, is an expensive and time-consuming task.

Thus, in a preferred embodiment, the nucleic acid probes are obtained by amplification of the template nucleic acids in the above-described template array. The template pool includes at least one nucleic acid that provides the amplification template for each of the nucleic acid sequences that are to be included in the nucleic acid affinity matrix. Thus, template arrays can include least about 50, preferably at least about 100, more preferably at least about 500, 1000, 5,000, 10,000, 50,000, 100,000, 500,000 and even at least about 1,000,000 different nucleic acid templates.

The nucleic acids can be amplified by any of the amplification methods well known in the art, which include, but are not limited to polymerase chain reaction (PCR) (Innis, et al., *PCR Protocols. a guide to Methods and Application.* Academic Press, Inc. San Diego, (1990)), ligase chain reaction (LCR) (see Wu and Wallace, *Genomics*, 4: 560 (1989), Landegren, et al., *Science*, 241: 1077 (1988) and Barringer, et al., *Gene*, 89: 117 (1990)), transcription amplification (see Kwoh, et al., *Proc. Natl. Acad. Sci.* (U.S.A.), 86: 1173 (1989)), and self-sustained sequence replication (see Guatelli, et al., *Proc. Nat. Acad. Sci.* (U.S.A.), 87: 1874 (1990)).

Amplification of the nucleic acids comprising the template pool can be performed in solution or with the template nucleic acids anchored to a solid support (e.g., a glass slide) and thereby forming a template array. In a preferred embodiment, amplification is by polymerase chain reaction (PCR). PCR amplification methods are well known to those of skill in the art. Basic amplification conditions can be found in a wide variety of references such as *PCR Protocols: a Guide to Methods and Applications,* Innis et al., eds. Academic Press, Inc. New York (1990).

One of skill will appreciate that amplification can be optimized for particular primer/template array combinations. Optimization typically involves adjusting magnesium ion concentration, buffer composition (e.g. KCl and NaCl ion concentration and buffer pH), and the temperature and length of time allowed for primer annealing, extension and denaturation. Methods of optimizing amplification protocols are routine and well known to those of skill in the art (see, e.g. Chapter 1 in *PCR Protocols: a Guide to Methods and Applications,* Innis et al., eds. Academic Press, Inc. New York (1990)). In a standard and suitable PCR protocol, the reaction mix includes about 20 pmol of each primer ($T_m$>55° C. preferred), 20 mM Tris-HCl (pH 8.3) (20° C.), 1.5 mM $MgCl_2$, 25 mM KCl, 0.05% TWEEN™-20, denaturing agent, 100 μg/ml autoclaved gelatin or nuclease-free bovine serum albumin, 50 μM each dNTP, and 2 units of Taq DNA polymerase.

The amplification is typically run through enough cycles to provide the desired amount of amplified product (capture probe). In a preferred embodiment, the amplification will be cycled enough to produce at least a 2 fold, generally at least a 5 fold, more generally at least a 10 fold, preferably at least a 100 fold, more preferably at least a 1000 fold, and most preferably at least a 10,000 fold amplification. Where most of the amplified nucleic acid pool is incorporated into the affinity matrix, the matrix will thus contain at least a 2 fold, generally at least a 5 fold, more generally at least a 10 fold, preferably at least a 100 fold, more preferably at least a 1000 fold, and most preferably at least a 10,000 fold more nucleic acid molecules of each species than the original nucleic acid template array.

A standard amplification will involve 20 to 40 cycles, more preferably about 25 to 35 cycles. In a preferred embodiment cycling is carried out for about 25 to about 35 cycles using the following temperature profile:

Denaturation: about 96° C., 15 seconds (a longer initial time is usually desirable);

Primer annealing; about 55° C., 30 seconds; and

Primer Extension: about 72° C., 1.5 minutes.

Cycling preferably concludes with a final extension at about 72° C. for 5 minutes. Reactions can be stopped by chilling to 4° C. and/or by addition of EDTA to 10 mM.

B) Post Amplification Processing.

While the amplified nucleic acid pool can be used directly, in a preferred embodiment, the amplified nucleic acids are purified away from reaction components (e.g. incomplete amplification products, nucleotide triphosphates, etc.). Means of purifying nucleic acid amplification products are well known to those of skill in the art. Typically the amplification products are the largest nucleic acids in the reaction mixture and purification techniques based on molecule size are highly effective. Such methods include, but are not limited to gel electrophoresis, high performance liquid chromatography (HPLC), affinity chromatography (e.g. using an affinity column complementary to the primer binding region), capillary electrophoresis, density gradient centrifugation, and the like. Particularly preferred is HPLC using an anion exchange column (e.g. mono Q from Pharmacia, Piscataway, New Jersey).

Where the amplified nucleic acids include restriction sites (e.g., for removal of the primer regions) and the amplified nucleic acids are to be cleaved at the reaction sites before use, the cleavage reaction can be performed before or after purification. However, in a preferred embodiment, it is desirable to cleave the amplification products prior to purification so that the desired cleaved product (e.g., capture probes) are purified away from the undesired sequences (e.g., primer binding regions) in the single purification step described above.

Cleavage of the amplified nucleic acids containing restriction sites is accomplished according to standard methods well known to those of skill in the art. Typically, the amplification product is combined with the restriction endonuclease specific for the cleavage site under conditions (e.g., temperature, pH) where the restriction endonuclease is active. Suitable reaction conditions for each particular restriction endonuclease are provided by the supplier or manufacturer.

3) Attachment of the Amplified Nucleic Acids to a Solid Support to Produce an Affinity Matrix.

The affinity matrices of this invention can be formulated with virtually any solid material or gel that does not substantially interfere with hybridization of the oligonucleotides. Suitable matrix materials include paper, glasses, ceramics, metals, metalloids, polacryloylmorpholide, various plastics and plastic copolymers such as Nylon™, Teflon™, polyethylene, polypropylene, poly(4-methylbutene), polystyrene, polystyrene, polystyrene/latex, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Materials that typically bind nucleic acids (e.g. cellulose) are suitable, however, in a preferred embodiment, an affinity matrix composed of such materials is preferably prehybridized with a blocking nucleic acid (e.g. sperm DNA or $C_0t$-1 DNA) to reduce non-specific binding.

The affinity matrix can be loaded with virtually any amount of oligonucleotide affinity ligand, the loading being only limited by available binding sites for attachment of the ligand and thus, only limited by the available amount of solid or gel support.

The affinity matrix can take any form that is convenient including beads, porous beads, crushed particles, membranes, tubing, planar surfaces, etc. Preferred matrix materials are particulate (e.g. beads) thereby providing increased surface area for attachment of affinity ligands. Particularly preferred matrix materials can be porous (fenestrated) highly convoluted and/or rugose (e.g. controlled pore glass, folded membranes, etc.).

Methods of attaching oligonucleotides to solid supports (matrix materials) are well known to those of skill in the art. For example, in a preferred embodiment, the primers used in the amplification can be provided with a conjugated biotin or streptavidin. The amplified nucleic acids will then bear the biotin or streptavidin and can be coupled to a solid support bearing avidin (streptavidin) or biotin respectively.

Alternatively, the nucleic acid can be covalently coupled to the solid support either directly via an activated group (e.g. a hydroxyl, a carboxyl) or through a linker that provides reactive moieties that bind to the oligonucleotide and to the matrix material respectively. Linkers suitable for attaching nucleic acids to matrix materials are also well known. Generally linkers are either hetero- or homo-bifunctional molecules that contain two or more reactive sites that may each form a covalent bond with the respective binding partner (the matrix material or the nucleic acid). For example, the probe oligonucleotides may be joined by a peptide linker, by a straight or branched chain carbon chain linker, or by a heterocyclic carbon. Heterobifunctional cross linking reagents such as active esters of N-ethylmaleimide have been widely used. See, for example, Lerner et al. *Proc. Nat. Acad. Sci.* (USA), 78: 3403–3407 (1981) and Kitagawa et al. *J. Biochem.*, 79: 233–236 (1976). Other linkers, such as those used in the synthesis of nucleic acids are also suitable (see, e.g. PCT Publication WO 85/01051, Pochet et al. *Tetrahedron.* 43: 3481–3490 (1987), Schwyzer et al., *Helv. Chim. Acta,* 67: 1316–1327 (1984), Gait, ed. *Oligonucleotide Synthesis: a Practical Approach,* IRL Press, Washington D.C. (1984)).

As indicated above, any material to which the oligonucleotide can be bound and which is resistant to nucleic acid hybridization reagents (e.g. Tris-HCl, SSC, etc.) and temperatures (e.g. 30° C. to 80° C.) and does not substantially interfere with the oligonucleotide hybridization is suitable for use as a matrix material. Particularly preferred matrix materials include glass beads, controlled pore glass, and various polymeric resins such as polystyrene, polystyrene/latex, and the like.

In a preferred embodiment, the amplified nucleic acids are purified away from the other components of the amplification mixture (e.g. triphosphates, truncated amplification products, etc.) prior to attachment to the matrix material. Methods of purifying nucleic acids are well known to those of skill in the art and described above in section 3.

IV. Hybridization Conditions.

The affinity matrices of this invention rely on hybridization between the nucleic acids comprising the affinity matrix and any target nucleic acids that may be present in the sample to specifically bind to and remove the target nucleic acids from the sample. Nucleic acid hybridization simply involves contacting the oligonucleotide probes of the affinity matrix and the target nucleic acid under conditions where the probe and its complementary target can form stable hybrid duplexes through complementary base pairing. The nucleic acids that do not form hybrid duplexes are then washed away leaving the hybridized nucleic acids bound to the affinity matrix. Where the bound nucleic acids are to be retrieved, the duplexes can be denatured (e.g. by increasing temperature, adding formamide or decreasing salt) and the freed nucleic acids recovered. Alternatively the sample contacted with the affinity matrix can be recovered and will be lacking those nucleic acids captured and removed by the affinity matrix.

It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency in this case in 6× SSPE-T at 37° C. (0.005% TRITON™ X-100 nonionic detergent) to ensure hybridization and then subsequent washes are performed at higher stringency (e.g., 1× SSPE-T at 37° C.) to eliminate mismatched hybrid duplexes. Successive washes may be performed at increasingly higher stringency (e.g., down to as low as 0.25× SSPE-T at 37° C. to 50° C.) until a desired level of hybridization specificity is obtained. Stringency can also be increased by addition of agents such as formamide. Hybridization specificity may be evaluated by comparison of hybridization to the sample nucleic acids with hybridization to the various controls that can be present (e.g., expression level control such as mRNAs spiked into the sample at known concentrations, etc.).

In general, there is a tradeoff between hybridization specificity (stringency) and signal intensity. Thus, in a preferred embodiment, the wash is performed at the highest stringency that produces consistent results or achieves maximum specific removal of the target nucleic acids from the sample.

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g., 8-mers) discriminate mismatches very well, but the overall duplex stability is low.

Altering the thermal stability ($T_m$) of the duplex formed between the target and the probe using, e.g., known oligonucleotide analogues allows for optimization of duplex stability and mismatch discrimination. One useful aspect of altering the $T_m$ arises from the fact that adenine-thymine (a-T) duplexes have a lower $T_m$ than guanine-cytosine (G-C) duplexes, due in part to the fact that the a-T duplexes have 2 hydrogen bonds per base-pair, while the G-C duplexes have 3 hydrogen bonds per base pair. In heterogeneous oligonucleotide matrices in which there is a non-uniform distribution of bases, it is not generally possible to optimize hybridization for each oligonucleotide probe simultaneously. Thus, in some embodiments, it is desirable to selectively destabilize G-C duplexes and/or to increase the stability of a-T duplexes. This can be accomplished, e.g., by substituting guanine residues in the probes of a matrix which form G-C duplexes with hypoxanthine, or by substituting adenine residues in probes which form a-T duplexes with 2,6 diaminopurine or by using the salt tetramethyl ammonium chloride (TMACl) in place of NaCl.

Altered duplex stability conferred by using oligonucleotide analogue probes can be ascertained by following, e.g., fluorescence signal intensity of oligonucleotide analogue arrays hybridized with a target oligonucleotide over time. The data allow optimization of specific hybridization conditions at, e.g., room temperature (for simplified diagnostic applications in the future).

Another way of verifying altered duplex stability is by following the signal intensity generated upon hybridization with a labeled sample with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature.

Methods of optimizing hybridization conditions are well known to those of skill in the art (see, e.g., *Laboratory Techniques in Biochemistry and Molecular Biology, Vol.* 24: *Hybridization With Nucleic Acid Probes,* P. Tijssen, ed. Elsevier, N.Y., (1993)).

In a preferred embodiment, the affinity matrix is packed into a columnar casing. The sample is then applied to the affinity matrix (e.g. injected onto a column or applied to a column by a pump such as a sampling pump driven by an autosampler). The affinity matrix (e.g. affinity column) bearing the sample is subjected to conditions under which the nucleic acid probes comprising the affinity matrix hybridize specifically with complementary target nucleic acids. Such conditions are accomplished by maintaining appropriate pH, salt and temperature conditions to facilitate hybridization as discussed above.

It is understood that the embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A nucleic acid amplification template array comprising a surface to which are attached at least 50 nucleic acid probes having different predetermined nucleic acid sequences and wherein:
   i) each different probe is localized in a known location of said surface;
   ii) the density of said probes is greater than about 60 different probes per 1 $cm^2$; and
   iii) said different probes have an identical terminal 3' nucleic acid sequence and an identical terminal 5' nucleic acid sequence, said identical terminal 3' and 5' nucleic acid sequence capable of serving as primer binding sites.

2. The template array of claim 1, wherein said 3' terminal nucleic acid sequence and said 5' terminal nucleic acid sequence each range in length from about 4 to about 30 nucleotides.

3. The template array of claim 1, wherein said 3' terminal nucleic acid sequence and said 5' terminal nucleic acid sequence are identical to each other.

4. The template array of claim 1, wherein said 3' terminal nucleic acid sequence and said 5' terminal nucleic acid sequence include a recognition site for a restriction endonuclease.

5. The template array of claim 1, wherein the different probes also each comprise a non-identical region, different probes having non-identical regions that differ in nucleotide sequence, and wherein non-identical regions of said probes range in length from about 10 to about 50 nucleotides.

6. The template array of claim 1, wherein the range of thermal melting points ($T_m$) of non-identical regions of said probes with sequences complementary to said non-identical regions is less than about 20° C.

7. A nucleic acid affinity matrix that reduces known nucleic acid molecules in a sample, said affinity matrix comprising a multiplicity of at least 20 different predetermined nucleic acid probes, wherein:
   there exists in said affinity matrix a probe complementary to each of said nucleic acid molecules or a subsequence thereof;
   said at least 20 different predetermined probes do not include every possible probe having the same length as said predetermined probes; and
   wherein the probes comprising said multiplicity of probes are preselected by the steps of:
   i) determining an allowable $T_m$ interval;

ii) determining a mismatch $T_m$ threshold;
iii) identifying all nucleic acid sequences of a preselected length complementary to a known nucleic acid molecule whose $T_m$ to said known nucleic acid molecule is within said allowable $T_m$ interval;
iv) determining the likelihood of each of said nucleic acid sequences complementary to said known nucleic acid molecule also occurring in an unknown message;
v) sorting said sequences in order of likelihood with the least likely sequence first;
vi) selecting the first nucleic acid sequence whose $T_m$ to all other known nucleic acid molecules in said sample is below said mismatch $T_m$;
vii) repeating step vi) until a desired number of nucleic acids that specifically hybridize, under stringent conditions, to said known nucleic acid molecule are obtained;
viii) repeating steps iii) through vii) until at least one nucleic acid sequence that hybridizes specifically under stringent conditions to each known nucleic acid molecule is selected.

8. The affinity matrix of claim 7, wherein said probes range in length from about 6 nucleotides to about 50 nucleotides.

9. The affinity matrix of claim 7, wherein said probes are present in approximately equimolar amounts.

10. The affinity matrix of claim 7, wherein step (vi) further comprises selecting the probe that additionally has a $T_m$ to all already selected nucleic acids below said mismatch $T_m$.

11. A nucleic acid affinity matrix that reduces known nucleic acid molecules in a sample, said affinity matrix comprising a multiplicity of at least 20 different predetermined nucleic acid probes, wherein:
   there exists in said affinity matrix a probe complementary to each of said nucleic acid molecules or a subsequence thereof; and
   said at least 20 different probes do not include every possible probe having the same length as said predetermined probes; and
   wherein said affinity matrix is prepared according to a method that comprises
   providing a nucleic acid amplification template array comprising a surface to which are attached at least 20 template nucleic acid probes having different predetermined nucleic acid sequences, wherein:
      i) each different template probe is localized in a known location of said surface;
      ii) the density of said template probes is greater than about 60 different template probes per 1 $cm^2$; and
      iii) said different template probes have an identical terminal 3' nucleic acid sequence and an identical terminal 5' nucleic acid sequence; and
   amplifying said multiplicity of oligonucleotides at least about 10 fold to provide a nucleic acid pool from which the at least 20 different predetermined nucleic acid probes are obtained.

* * * * *

UNITED STATES PATENT AND TRADEMARK OFFICE
CERTIFICATE OF CORRECTION

PATENT NO. : 6,280,950 B1
DATED : August 28, 2001
INVENTOR(S) : Lipshutz et al.

It is certified that error appears in the above-identified patent and that said Letters Patent is hereby corrected as shown below:

Title page,
Item [63] "Related U.S. Application Data" should read as follows:

-- Division of application No. 08/815,395, filed on Mar. 10, 1997, now Pat. No. 6,013,440 --

Signed and Sealed this

Fourteenth Day of May, 2002

*Attest:*

*Attesting Officer*

JAMES E. ROGAN
*Director of the United States Patent and Trademark Office*